(12) United States Patent
Kratz et al.

(10) Patent No.: US 6,187,971 B1
(45) Date of Patent: Feb. 13, 2001

(54) METHOD FOR PRODUCING POLYALCOHOLS

(75) Inventors: Detlef Kratz, Heidelberg; Achim Stammer, Freinsheim; Gerhard Schulz, Ludwigshafen; Guido Voit, Schriesheim, all of (DE)

(73) Assignee: BASF Aktiengesellschaft, Ludwigshafen (DE)

( * ) Notice: Under 35 U.S.C. 154(b), the term of this patent shall be extended for 0 days.

(21) Appl. No.: 09/331,370
(22) PCT Filed: Dec. 4, 1997
(86) PCT No.: PCT/EP97/06776
 § 371 Date: Jun. 21, 1999
 § 102(e) Date: Jun. 21, 1999
(87) PCT Pub. No.: WO98/28253
 PCT Pub. Date: Jul. 2, 1998

(30) Foreign Application Priority Data

Dec. 20, 1996 (DE) .............................................. 196 53 093

(51) Int. Cl.$^7$ ................................................... C07C 31/18
(52) U.S. Cl. ........................... 568/853; 568/457; 568/464
(58) Field of Search ................................... 568/853, 457, 568/464

(56) References Cited

U.S. PATENT DOCUMENTS

| 3,808,280 | * | 4/1974 | Merger ................................. 568/853 |
| 4,594,461 | * | 6/1986 | Merger ................................. 568/853 |
| 4,740,639 | * | 4/1988 | Beavers ................................ 568/853 |
| 4,851,592 | * | 7/1989 | Morris ................................. 568/853 |
| 5,072,058 | * | 12/1991 | Dambkes ............................. 568/853 |
| 5,185,478 | * | 2/1993 | Salek .................................. 568/583 |
| 5,532,417 | * | 7/1996 | Salek .................................. 568/853 |
| 5,763,690 | * | 6/1998 | Salek .................................. 568/853 |

* cited by examiner

Primary Examiner—Michael L. Shippen
(74) Attorney, Agent, or Firm—Keil & Weinkauf

(57) ABSTRACT

Methylolalkanal of the formula II

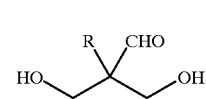

(II)

(R=CH$_2$OH, C$_1$–C$_{22}$-alkyl, aryl or C$_6$–C$_{22}$-aralkyl) is prepared spe-wise by
 a) reacting a C$_2$–C$_{24}$-aldehyde with formaldehyde in the presence of a tertiary amine,
 b) separating the reaction mixture
  i) into a bottom fraction comprising the compound of formula II and an incompletely methylolated compound of the formula III

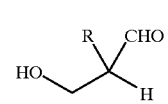

(III)

and a distillate stream comprising unconverted or partially converted starting materials, or
  ii) into an aqueous phase and an organic phase, and recycling the distillate stream or the organic phase to a), and
 c) subjecting the bottom fraction or the aqueous phase
  i) to a catalytic or thermal reaction to convert the compound of formula III to the compound of formula II and to a corresponding methylene compound of formula IV

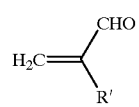

(IV)

(R'=H or R) and
  ii) separating the reaction product into an overhead stream comprising the compound of formula IV and unconverted formaldehyde which is recycled to a), and a bottom fraction comprising the compound of formula II.

15 Claims, 4 Drawing Sheets

METHOD FOR PRODUCING POLYALCOHOLS

The invention relates to a process for the preparation of geminate polymethylol compounds by condensation of aldehydes with formaldehyde and hydrogenation of the resulting polymethylolalkanals, without the formation of formates by coupling.

PRIOR ART

Processes Involving the Formation of a Coupling Product

Trimethylol propane (TMP) is usually prepared industrially by the so-called inorganic Cannizzaro process. In this case n-butyraldehyde (n-BA) is caused to react with excess formaldehyde (FA) in the presence of stoichiometric amounts of inorganic base such as NaOH or Ca(OH)$_2$. Not only TMP is formed by the Cannizzaro reaction but also one equivalent of sodium or calcium formate. The occurrence of an inorganic salt as coupling product has varied drawbacks. Firstly the separation of the salt of TMP is complicated and involves additional expenditure; secondly the inorganic salt—if it is to be utilized to good effect—must be worked up and purified: and thirdly the occurrence of a coupling product signifies a loss of the stoichiometric amounts of sodium hydroxide solution and formaldehyde used. Furthermore, the yields obtained in this inorganic Cannizzaro reaction, including those of the butyraldehyde, are unsatisfactory, since high-boiling components are formed during the reaction which cannot be utilized.

Similar problems to those stated for TMP relate to the preparation of other triols such as trimethylol ethane (from n-propanal and formaldehyde) or trimethylolbutane (from n-pentanal and formaldehyde). Like TMP these triols are prepared by the inorganic Cannizzaro process with formation of an inorganic salt by coupling. The same applies to the preparation of pentaerythritol from acetaldehyde and formaldehyde. Trimethylol propane, trimethylol ethane and trimethylolbutane are polyols which are used in the plastics industry in a variety of ways for the preparation of varnishes, urethanes and polyesters. Pentaerythritol is a frequently used intermediate in the paints and varnishes industry and is also useful for the preparation of explosives (pentaerythritol tetranitrate).

The reaction of n-BA with FA in the presence of a tert-amine in one improved process is described in DE-A 1,952.738. The stoechiometry of N-BA:FA of approximately 1:6 and the use of superstoichiometric amounts of the amine have however the result that not only TMP but also stoichiometric amounts of trialkylammonium formate are produced. Amine and the formic acid formed are removed by distillation as organic salt and must thus be processed and recovered, in order to make the process economical. The amines used were triethylamine and trimethylamine.

One way of avoiding the occurrence of organic salt (trialkylammonium formate) is described in EP-A 0,142, 090, EP-A 0,289,921 and in the German patent applications having the file numbers P 19542035.7 and P19542036.5. Said references also describe the use of stoichiometric amounts of a trialkylamine of an inorganic base as base. The trialkylammonium formate formed as coupling product is converted to methyl formate during the process. The advantage of this organic Cannizzaro process over the inorganic variant is the increased yield. But a disadvantage thereof is the fact that here again a coupling product (methyl formate) is formed and thus one equivalent of formaldehyde more than is necessary is consumed in the process.

Thus a process for the preparation of TMP without the formation of any sort of coupling product is desirable from an economic standpoint.

Processes Without the Formation of a Coupling Product

According to the statements made in DE-A 2,507,461 dimethylolbutanal (DMB) can be prepared by the reaction of n-butyraldehyde (n-BA) with formaldehyde (FA) in the presence of catalytic amounts of a tert-amine via the intermediate monomethylolbutanal (MMB) (equation 1). Subsequent hydrogenation gives TMP (equation 2).

Equation 1:

(n–BA)    (FA)

(MMB)    (FA)

(DMB)

Equation 2:

(DMB)    (TMP)

The hydrogenation of the dimethylolbutanal (DMB) formed as intermediate from n-BA and FA to form TMP is also described in DE-A 25 07 461. The same specification reveals that the elimination of water from the resulting intermediate monomethylolbutanal (MMB) causes the formation of the by-product ethylacrolein (EA). The possibility of utilizing EA via its reverse reaction in the presence of water (equation 3), is explained in example 5.

Equation 3

(EA)    (MMB)

(DMB)

The yields of DMB given in the examples are approximately 85%; the TMP yields following hydrogenation are said to be 75% (based on n-BA), whilst yields based on FA are given.

The process of this patent specification has the drawback that use must be made of specific branched-chain tert-amines (eg. dimethylaminoneopentanolamine), which are not available in commercial amounts. Using industrially available amines such as triethylamine worse yields are observed (57% of TMP based on n-BA). The branched-chain amine is not recycled in the said process, which thus keeps the costs of the process high. Neither is unconverted n-BA or FA recycled to the process.

Another variant is described in DE-A 2,702,582, in which use is made of formaldehyde in an excess of at least 8 times over the aldehyde for aldolization in the presence of tert-amines in combination with alkali metal or alkaline earth metal compounds at from −5° to 0° C. The aldol product formed is then hydrogenated to TMP. The bases used are linear tert.-amines. In the majority of the examples inorganic bases are additionally used. The yield obtained when only triethamine is used (example 5, n-BA:FA:NEt$_3$=1:10:0.18) is 74.6% of TMP.

This process is based on the use of a large excess of formaldehyde and low temperatures. Large amounts of FA, however, are a contributary factor in the formation of FA adducts of the alcohol components that are present in the reaction mixture (formation of acetals and hemiacetals of FA with DMB and MMB). This in turn leads to an unfavorable yield based on FA used. The use of inorganic reageants for the aldolization gives rise to additional problems when purifying the TMP by distillation. The maintenance of low temperatures (−5° to 0° C.) calls for additional plant requirements. A total of 18 mol % of tert-amine is used which is not recycled to the process.

The processes of DE-A 2,813,201 and DE-A 2,702,582 also both involve a high excess of formaldehyde, and an acceptable yield based on n-butyraldehyde is achieved only at the expense of formaldehyde used, so that these processes are also uneconomical.

DE-A 2,714,516 describes the reaction of ethylacrolein (EA) with formaldehyde (FA) in a ratio of EA:FA of from 1:8 to 1:30 in the presence of basic catalysts. The yield of DMB is stated to be 90% based on EA. However, the yield based on FA is only 12%.

Here again the process is not economical by reason of the large amounts of FA and trialkylamine catalyst used.

It is thus an object of the present invention to provide a process which produces polymethylol compounds, eg trimethylol propane from n-butyraldehyde and formaldehyde, in high yields based on n-butyraldehyde and formaldehyde and without the formation of a coupling product. This process should be equally well suited for the preparation of other polyalcohols from the higher and lower homologous alkanals of n-butyraldehyde.

This object is achieved in a process for the preparation of polymethylol compounds of formula I in which R denotes another methylol group or an alkyl group containing from 1 to 22 carbon atoms or an aryl or aralkyl group containing from 6 to 22 carbon atoms, by condensation of aldehydes containing from 2 to 24 carbon atoms with formaldehyde using tertiary amines as catalyst to form compounds of formula II in which R has the meaning specified above and the hydrogenation thereof, characterized in that the condensation is carried out step-wise by
    a) causing the aldehydes containing from 2 or more carbon atoms to react, in a first (reaction) stage, with 2 to 8 times the molar amount of formaldehyde in the presence a tertiary amine acting as catalyst,
    b) either separating the reaction mixture, in a second (separating) stage) into bottoms predominantly containing the compounds of formula II and a distillate stream predominantly comprising unconverted or partially converted starting materials, which is recycled to the first stage, or separating the reaction mixture from the first stage by means of a phase-separating equipment into an aqueous and an organic phase and recycling the organic phase to the first stage, and
    c) subjecting, in a third stage (post-reaction stage) the bottoms from the second stage or the aqueous phase obtained in the second stage by phase separation to a catalytic and/or thermal treatment, whilst the incompletely methylolated compound of formula III converts to the corresponding compound of formula II and to the corresponding methylene compound of formula IV in which R' is hydrogen or has the meaning stated for R above, and recycling the overheads of this distillation operation, which contain a compound of formula IV and unconverted formaldehyde, to the first stage and hydrogenating, in known manner, the bottoms of said distillation containing substantially the compound of formula II to the corresponding end product of formula I.

For the purposes of the present description of the process of the invention, the expression "first (reaction) stage" is taken to be synonymous with "reaction stage", "first stage", or "stage a)", the expression "second (separating) stage" is taken to be synonymous with "separating stage", "second stage", or "stage b)", whilst the expression "third (post-reaction/distillation) stage is taken to be synonymous with "post-reaction/distillation stage", "third stage", or "stage c)".

In a preferred embodiment the recycled distillates or the recycled organic phase obtained by phase separation in the second stage, are, if they contain substantial amounts of methylene compounds of formula IV, subjected to a preliminary reaction with formaldehyde and tertiary amine before they are brought into contact with further aldehyde containing from 2 or more carbon atoms.

In another preferred embodiment the distillate or the distillate streams of the second stage are subjected to a subsequent thermal reaction and again distilled and the distillate obtained or, if this operation is repeated a number of times, the last distillate is recycled to stage a).

Thus preferred embodiments of the present process primarily consist in the use of a preliminary reaction of the distillate containing methylene compounds of formula IV with formaldehyde and/or optionally in the execution of a subsequent catalytic and/or thermal reaction of the distillates before they are recycled to the first stage and/or optionally in the execution of a subsequent catalytic and/or thermal reaction of the aqueous bottoms obtained in the distillation (s). An alternative preferred embodiment consists in recycling the organic phase obtained in the separating stage by phase separation and the preliminary reaction thereof with formaldehyde and/or optionally in the execution of a subsequent catalytic and/or thermal reaction of the aqueous phase obtained in the separating stage by phase separation.

The process of the invention involves in particular a reaction scheme which allows for the quantitative conversion of aldehyde used and the quantitative conversion of methylene compounds of formula IV formed as intermediates to produce the compounds of formula II. Thus the catalytic and/or thermal post-treatment in stage c) of the process of the invention and recycling of the resulting distillate to stage a) results in particularly advantageous utilization of the starting materials used. Consequently, stage a) involves treatment of the reactants aldehyde and FA, on the one hand, and also of the recycled streams coming from the stages b) and c) and containing aldehyde, methylene compound of formula IV, formaldehyde, water and amine catalyst, on the other hand.

Surprisingly, these streams can be re-used quantitatively in the reaction without any undesirable secondary components being produced. Trouble-free recycling of these streams is achieved particularly well if the reaction is carries out such that these streams are first of all caused to react in an upstream reactor with fresh FA, after which the reaction of the resulting mixture with the other starting compounds is carried out in stage a). This method of "staggered addition" of the reactants leads to considerably better yields than in the prior art.

An important feature of the process of the invention consists in the subsequent reaction of the distillation bottoms or the aqueous phase obtained in the separating stage by phase separation still containing monomethylolized or, in the case of acetaldehyde, mono and dimethylolized intermediates, which by this means are converted prior to hydrogenation into the relevant completely methylolated compound and the relevant compound of the general formula IV. This takes place either in a separated post-reactor, optionally with the further addition of tertiary amine, or in a reaction column or in a combination of both possibilities.

The novel process may be carried out batchwise or continuously.

BRIEF DESCRIPTION OF DRAWINGS

The general principle of the present process is schematically shown in FIG. 1.

To illustrate the general principle of the process it is described below with reference to FIG. 1 which is a diagrammatic representation of the preparation of TMP.

In the first (reaction) stage 1, which can comprise a single reactor or a number of reactors, preferably a tubular reactor or a cascade of stirred vessels, the starting materials n-BA and FA, preferably introduced in the form of an aqueous solution, and also the tert-amine catalyst, which are fed in via the feed pipes 2, 3 and 4 respectively are caused to react to produce a mixture of the compounds DMB and MMB which in addition contains, as main components, unconverted n-BA, FA and EA and also the amine catalyst and possibly water. Via pipe line 5, this mixture is fed to the (separating) stage, in this case the distilling apparatus 6, for example a column or a thin-layer evaporator, in which the mixture is separated by distillation into readily volatile and less readily volatile components. As a result of suitable adjustment of the distillation conditions in 6 there is formed a fraction consisting of low-boilers which contain, as essential components, unconverted n-BA and FA, water and part of the amine catalyst, and also EA which is already present in the effluent from the (reaction) stage and is additionally formed by elimination of water from MMB under the distillation conditions. This low-boiling fraction is recycled through pipe line 7, following condensation thereof in a condenser (not shown), to the (reaction) stage 1. The poorly volatile bottoms obtained in the distillation 6, which substantially comprise DMB, MMB and part the amine catalyst, pass through pipe line 8 to the (post-reaction/distillation) stage 9, into which, if desired, additional fresh FA and amine catalyst are passed through the pipe lines 14 and 15.

The (post-reaction/distillation) stage 9 can consist of one or, preferably, more than one stirred boilers or one or more tubular reactors followed by a distillation plant, eg a column or a thin-layer evaporator or Sambay evaporator. In stage 9 the residual MMB is converted to DMB and the resulting reaction mixture is subsequent concentrated by separation of the low-boilers water, FA, EA and amine catalyst by distillation. These low-boilers are recycled through pipe line 10 to the (reaction) stage 1, whereas the less volatile DMB is fed through pipe line 11 to the hydrogenating reactor 12, where it is catalytically hydrogenated in conventional manner with hydrogen (inlet not shown) to form TMP, which is withdrawn via pipe line 13. If necessary, the effluent from the hydrogenating reactor can be subjected to purifying distillation. The streams recycled through the pipe lines 7 and 10 and comprising unconverted starting materials, amine catalyst, water and the intermediate EA are again caused to react in the (reaction) stage 1 together with the freshly introduced starting materials in the manner described above. The feed of fresh starting materials and optionally fresh catalyst is advantageously controlled by suitable conventional regulating means such that a steady state is established in 1. Any water continuously introduced in the form of an aqueous FA solution can be removed via pipe line 16. Such removal of water is not necessary for successfully accomplishing the process of the invention, but it has the advantage that the volume of DMB solution to be hydrogenated in the hydrogenating reactor 12 is reduced. The water can, of course, be separated by distillation after it has left the hydrogenating reactor 12.

Since the compounds recycled to 1 through pipe lines 7 and 10 are caused to react therein under steady-state equilibrium conditions with virtually no formation of by-products, the overall balance of the process of the invention shows virtually quantitative conversion of the starting materials and a selectivity toward the formation of TMP of more than 90%, based on butyraldehyde.

Alternatively to the method of operation described above, it is possible to carry out the process of the invention advantageously in such a manner that the reaction mixture forming the effluent from (reaction) stage 1 through pipe line 5 is passed to a phase-separating apparatus 6a instead of the distillation plant 6, in which phase-separating equipment the two-phase effluent is separated into an aqueous and an organic phase. This operating method is particularly advantageous when the reaction mixture from reaction stage 1 exists in two liquid phases, which is usually the case. If, however, the effluent from 1 is in a homogeneous liquid form, two phases can be created therefrom by, say, the addition of water. Since a quantitative separation of the organic and aqueous phases in the phase-separating equipment 6a of the (separating) stage is not necessary for successfully accomplishing the process of the invention, no special technical demands are placed on the type of phase-separating apparatus to be used, ie it can be phase-separating equipment such as is usually employed for liquid/liquid separations, as described in Ullmanns Encyklopaedie der technischen Chemie, 4th Edition, Vol. 2, pp 560 to 565, Verlag Chemie, Weinhein 1972, eg settling tanks, centrifuges or columns containing baffles to improve phase separation, such as sieve tray columns or packed columns or columns containing rotating baffles.

The organic phase obtained by phase separation and containing, as essential components, EA, unconverted butyraldehyde and minor amounts of amine catalyst, FA, MMB, water and DMB is recycled to the (reaction) stage 1 and the aqueous phase containing, as essential components, DMB, minor amounts of MMB and also FA and amine catalyst is fed to the (post-reaction/distillation) stage 9. As a result, when phase-separating equipment 6a is used instead of distilling apparatus 6 the organic phase obtained by the phase separation is further treated in the later process steps in a manner similar to that described for the low-boilers and the aqueous phase in a manner similar to that described for the high-boiling bottoms obtained when distilling apparatus 6 is used.

Figure 1:
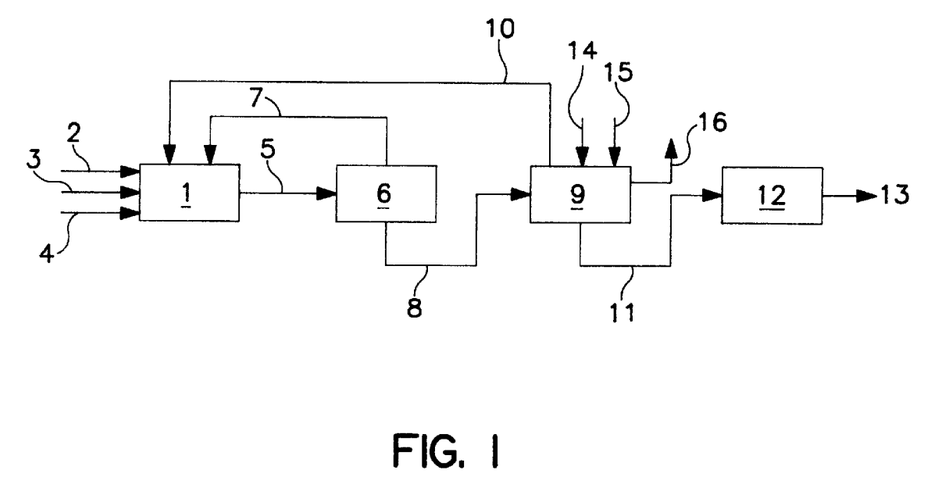
Figure 2:
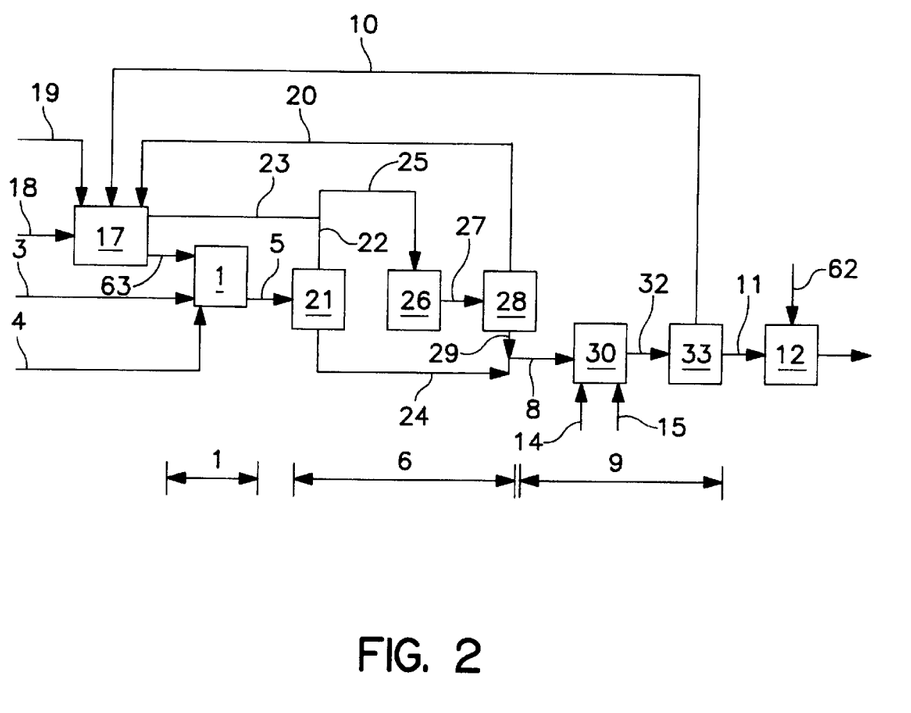
FIG. 2 diagrammatically illustrates a particular embodiment of the process.

Specifically, the process of the invention is advantageously carried out in a manner diagrammatically illustrated with regard to preferred and/or alternative embodiments with reference to FIG. 2 for example for the preparation of TMP from n-BA and FA. Where equipment in FIG. 2 directly corresponds to equipment in FIG. 1 the same reference numerals are used.

In the preceding reactor 17, for the purposes of this application referred to simply as the "upstream reactor", to which there is metered via the pipe lines 18 and 19, fresh FA, preferably in the form of an aqueous solution and, when necessary for establishing steady operating conditions during continuous operation of the process, fresh tert-amine catalyst, the low-boilers containing unconverted n-BA and FA, and also EA formed, in addition water and amine catalyst as essential components and recycled through the pipe lines 20 and/or 23 from the (separating) stage 6, according to FIG. 1, and the FA/water mixture which possibly also contains amine catalyst and is recycled through pipe line 10 from the (post-reaction/distillation) stage 9, according to FIG. 1, are caused to react.

In the upstream reactor 17 the educts may be present in the following molar ratios for example: the molar ratio n-BA:EA can vary greatly depending on the controlled n-BA conversion or the reflux ratio set in the distilling apparatus 21 and 28 and is between 1:1000 and 1000:1; the molar ratio (n-BA+EA):FA is generally from 1:0.01 to 1:50, preferably from 1:2 to 1:20 and the amount of tertiary amine used is usually such that the pH of the reaction mixture is from 5 to 12, preferably from 6 to 11.

The overall concentration of the solution of the organic components in water in the upstream reactor 17 is generally from 5 to 60 wt %, preferably from 10 to 45 wt %. The reaction is generally carried out at a temperature of from 5 to 100° C. and preferably at from 15 to 80° C., and the residence time is generally maintained at from 0.25 to 12 hours depending on the temperature. The effluent from the upstream reactor 17, which contains, as essential components, unconverted FA and n-BA, EA, MMB and DMB and also the amine catalyst and water, is fed through pipe line 63 to the (reaction) stage 1, which can be a stirred boiler, a tubular reactor or preferably a cascade of stirred vessels. To the (reaction) stage 1 there is metered through pipe line 3 fresh n-BA and, if necessary for the regulation of the steady-state equilibrium or the pH in 1, additional amine catalyst through pipe line 4. When a cascade of stirred vessels is used, metering of the fluids may be effected such that either only the first stirred vessel of the cascade or some or all of the stirred vessels in the cascade is/are charged with n-BA or the tert.-amine via pipe lines 3 and 4 respectively. The tert-amine is usually added at such a rate that the pH is again from 5 to 12 and preferably from 6 to 11. When a tubular reactor is used, the amine catalyst can be replenished at various points along the tube in order to keep the pH at the desired value over the entire length of the reaction tube. The molar ratio of freshly introduced n-BA in 1 to the amount of FA added in the upstream reactor 17 is advantageously between 1:2 and 1:5, preferably between 1:2 and 1:3.5. The FA present in excess in the effluent from the upstream reactor 17 reacts in (reaction) stage 1 with n-BA to form, substantially, DMB. The amount of tert-amine catalyst fed to the upstream reactor 17 and the reaction stage 1 is usually from 0.001 to 0.2, preferably from 0.01 to 0.07, equivalents based on the n-BA charged to the (reaction) stage 1, that is to say, the amine is used in catalytic quantities. The overall concentration of the organic components in the aqueous reaction mixture is generally from 5 to 60 wt % and preferably from 10 to 45 wt %. The reaction is generally carried out at a temperature of from 5 to 100° C., preferably from 15 to 80° C. and the residence time is generally maintained at from 0.25 to 12 hours depending on the temperature.

The effluent from (reaction) stage 1, which substantially contains DMB, minor amounts of MMB and EA, excess FA, small amounts of unconverted n-BA, water and amine catalyst, is fed through pipe line 5 to the (separating) stage 6 which can be designed as explained with reference to FIG. 1 or alternatively, can be configured as described below, where all of the equipment embraced by the brackets marked 6 in FIG. 2 is to be regarded as comprising the apparatus and reactors, defined as belonging to the (separating) stage b), equivalent to (separating) stage 6 of FIG. 1.

The effluent from (reaction) stage 1, on entering the (separating) stage 6, is first of all passed through pipe line 5 to the distilling apparatus 21 which may be, eg, a column, a thin-layer evaporator or a Sambay evaporator, in which the effluent from 1 is separated by distillation into low-boilers which are removed as overheads or from the upper part the distilling apparatus 21, and high-boilers, which are formed as bottoms or are withdrawn from the lower part the distilling apparatus 21. Distillation is carried in conventional manner generally at from 50 to 200° C. and preferably from 90 to 160° C. and at a pressure of from 0.1 mbar to 10 bar and preferably from 0.5 to 5 bar, in particular under atmospheric pressure.

The low-boilers leaving as overheads or withdrawn from the upper part of the distilling apparatus 21 via pipe line 22 contain, as essential components, unconverted n-BA and FA, EA and water and amine catalyst, whilst the high-boilers withdrawn from the base or lower part of the distilling equipment 21 through pipe line 24 contain, as essential components, DMB, a small amount of MMB and residual amounts of water, FA and amine catalyst. The concentration of DMB in the high-boiling product removed from 21 is generally from 5 to 90 wt %. The high-boiling mixture in the distilling apparatus 21 is fed through the pipe lines 24 and 8 to the (post-reaction/distillation) stage 9, whereas the low-boiler mixture may be recycled, completely or as a partial stream, through the pipe lines 22 and 23 to the upstream reactor 17 and/or fed through the pipe lines 22 and 25, after condensation, to the reactor 26, which can be, eg, a stirred boiler, a cascade of stirred vessels or a tubular reactor, where it is subjected to a subsequent reaction at generally from 10 to 100° C., preferably from 15 to 80° C., for a period generally of from 0.25 to 12 hours, during which subsequent reaction the amine catalyst present in the distillate causes the reaction of components n-BA, EA and FA present in the distillate, to form DMB and MMB. The effluent from the post-treatment reactor 26 is fed through pipe line 27 to the distilling equipment 28, in which, in a manner similar to that described with reference to the distillation in the distillation equipment 21, there occurs separation, by distillation, of low-boilers and high-boilers, the low-boilers passing through pipe line 20 back to the upstream reactor 17 and high-boilers passing through pipelines 29 and 8 to the (post-reaction/distillation) stage 9.

The aforementioned sequence of operations comprising post-reaction/distillation of the low-boiler distillate from distilling apparatus 21 can be repeated a number of times, if desired, within the scope of the (separating) stage b), equivalent to the (separating) stage 6 of the drawings. This post-reaction/distillation sequence within the (separating) stage 6 can comprise an alternative to or supplement of, direct recycling of the low-boilers from distilling apparatus 21 through the pipe lines 22 and 23 to the upstream reactor 17, which can be equally as good as, or better than, direct recycling, depending on the type of polymethylol compound to be synthesized. Recycling of the low-boilers from (separating) stage 6 to the upstream reactor 17 is an advantageous embodiment of the process of the invention; and of course, the low-boiler streams recycled from the (separating) stage 6 can be recycled completely or as partial streams directly to the (reaction) stage a), equivalent to (reaction) stage 1 of the drawings, if desired.

Depending on which of the aforementioned embodiments of the process of the invention is used, either the high-boilers coming from the distilling apparatus 21 via the pipe lines 24 and 8 or the high-boilers coming from the distilling apparatus 21 and 28 and combined via the pipe lines 24 and 29 are passed through pipe line 8 to the post-treatment reactor 30 of the (post-reaction/distillation) stage c), equivalent to the (post-reaction/distillation) stage 9 in the drawings, for the purpose of completing the reaction of the MMB present in the high-boiler mixture with FA to form DMB.

If there is used, instead of the distilling apparatus 21 in the embodiment described with reference to FIG. 2, phase-separating equipment 21a, the organic phase obtained in the phase separation, whose chemical composition is approximately the same as that described with reference to FIG. 1, can be treated in the later stages of the process in a manner similar to that described for the low-boilers obtained using a distilling apparatus 21, and the aqueous phase obtained in the phase separation in 21a can be processed in later stages of the process in a manner similar to that described with reference to the high-boiling bottoms obtained using a distilling apparatus 21.

In the post-treatment reactor 30, which may be, say, a stirred boiler or preferably a cascade of stirred vessels or a tubular reactor, the high-boiler mixture is heated for a period of generally 0.1 to 5 hours, preferably of 0.5 to 3 hours, to generally 30 to 200° C., preferably 40 to 150° C.

The amine catalyst still present in catalytically effective amounts in the high-boiler mixture causes virtually complete reaction of MMB with the FA still present in the high-boiler mixture or any further FA separately added via pipe-line 15, to produce DMB. A portion of the FA in the high-boiler mixture exists in the form of hemiacetals bonded to MMB and DMB, from which it is liberated during the course of said catalytic and/or thermal post-treatment, which makes it again available for the conversion of MMB to DMB. The above post-treatment and subsequent reaction of the high-boilers in the reactor 30 can be accelerated and, if desired, carried out under milder conditions, if a base, preferably the amine catalyst used during the aldolization, is added to the high-boiler mixture through pipe line 14a to adjust the pH to from 5 to 12, preferably from 6 to 11, following which the said high-boiler mixture is treated in the aforementioned temperature range. Instead of a low molecular weight tertiary amine, the base used for this purpose may be a polymeric tert-amine, for example a basic ion exchanger.

The effluent from the post-reacting reactor 30 is passed through pipe line 32 to a distilling apparatus 33, for example a thin-layer evaporator or a Sambay evaporator, where it is separated, by distillation, into high-boiling DMB and low-boilers containing, as essential components, FA, water, amine catalyst and possibly freshly formed EA, the low-boilers withdrawn as overheads or from a point in the upper part of the distilling apparatus being recirculated through pipe line 10 to, say, the upstream reactor 17 and/or, if desired, directly to the (reaction) stage 1, and the high-boiling DMB from the base or lower part of the distilling apparatus 33 being fed through pipe line 11 to the hydrogenating reactor 12, to which hydrogen is fed through pipe line 62. If desired, the distillation can be carried out in such a manner that a partial stream containing essentially water is condensed and removed.

The high-boiler product now containing almost exclusively DMB as reaction product from 33, whose content of DMB is 20 to 95 wt %, preferred 30 to 75 wt %, is catalytically hydrogenated in the hydrogenating reactor 12. Suitable hydrogenation catalysts are particularly copper-containing supported catalysts such as are described in, eg, WO 95/32171. Other suitable catalysts are those such as are described in EP-A 44,444, EP-A 44,412 or DE-A 1,957,592. Advantageously, the hydrogenation takes place continuously in, eg, a reactor tube packed with a catalyst bed, where the reaction solution passes through the catalyst bed eg in trickling mode or under transition flow conditions, as is described in DE-A 1,941,633 or DE-A 2,040,501. It may be advantageous to recycle a partial stream of the effluent, optionally with cooling, and pass this through the fixed catalyst bed once more. It may also be advantageous to carry out the hydrogenation in a number of in-line reactors, for example in 2 to 4 reactors, the hydrogenation be effected in the separate reactors, except for the last reactor, to a extent of only a partial conversion of, say, from 50 to 98% whilst only in the last reactor is the hydrogenation carried to completion. In this case it can be advantageous to cool the hydrogenation effluent from one reactor before it enters the following reactor, for example by means of cooling equipment or by injecting cold gases, such as hydrogen or nitrogen or introducing a partial stream of cold reaction solution.

The hydrogenation temperature is generally between 50 and 180° C., preferably between 90 and 140° C. The pressure applied for the hydrogenation is generally from 10 to 250 bar, preferably from 20 to 120 bar.

The hydrogenation can be carried out with the addition of an inert solvent. Suitable solvents are cyclic ethers, such as THF or dioxane, as also are acyclic ethers as well as lower alcohols, eg methanol, ethanol or 2-ethylhexanol.

In other respects, any suitable hydrogenating method can be used and hydrogenation catalysts employed such as are commonly used for the hydrogenation of aldehydes and described in the standard literature. The crude TMP thus obtained can be purified in conventional manner by distillation (not shown).

The process of the invention can be carried out with or without the addition of organic solvents or solubilizers. The addition of solvents or solubilizers can prove to be advantageous especially when long-chain aldehydes are used as starting materials. The use of solvents which form suitable, low-boiling azeotropic mixtures with the low-boiling compounds during the separate distillation stages of the process of the invention may possibly lower the energy consumed during such distillations and/or facilitate the separation, by distillation, of the low-boilers from the high-boiling compounds.

Examples of suitable solvents are cyclic and acyclic ethers such as THF, dioxane, methyl tert-butyl ether or alcohols such as methanol, ethanol or 2-ethylhexanol. The reactions carried out in the upstream reactor, the (reaction) stage, the (separating) stage and the (post-reaction/distillation) stage and described above in detail can be effected under a pressure generally of from 1 to 30 bar, preferably 1 to 15 bar, more preferably 1 to 5 bar, and advantageously under the autogenous pressure of the relevant reaction system.

The novel process can be applied to virtually all alkanals containing a methylene group in α-position relative to the carbonyl group. Aliphatic aldehydes containing from 2 to 24 carbon atoms can be used as starting materials. It is also possible to use aralphatic aldehydes as starting materials provided they contain a methylene group in α-position relative to the carbonyl group. Aralkylaldehydes containing from 8 to 24 carbon atoms, preferably those containing from 8 to 12 carbon atoms, are generally used as starting materials, for example phenylacetaldehyde. Preferred compounds are aliphatic aldehydes containing from 2 to 12 carbon atoms, for example 3-ethyl, 3-n-propyl, 3-isopropyl, 3-n-butyl, 3-iso-butyl, 3-sec-butyl, 3-tert-butylbutanal and also corresponding n-pentanals, n-hexanals, n-heptanals 4-ethyl, 4-n-propyl, 4-isopropyl, 4-n-butyl, 4-isobutyl, 4-sec-butyl, 4-tert-butyl pentanal, and the corresponding n-hexanals, n-heptanals, 5-ethyl, 5-n-propyl, 5-isopropyl, 5-n-butyl, 5-isobutyl, 5-sec-butyl, 5-tert-butyl n-hexanals and the corresponding n-heptanals, 3-methylhexanal, 3-methylheptanal 4-methylpentanal, 4-methylheptanal, 5-methylhexanal, 5-methylheptanal 3,3,5-trimethyl-n-pentyl, 3,3-diethylpentyl, 4,4-diethylpentyl, 3,3-dimethyl-n-butyl, 3,3-dimethyl-n-pentyl, 5,5-dimethylheptyl, 3,3-dimethylheptyl, 3,3,4-trimethylpentyl, 3,4-dimethylheptyl, 3,5-dimethylheptyl, 4,4-dimethylheptyl, 3,3-diethylhexyl, 4,4-dimethylhexyl, 4,5-dimethylhexyl, 3,4-dimethylhexyl, 3,5-dimethylhexyl, 3,3-dimethylhexyl, 3,4-diethylhexyl, 3-methyl-4-ethylpentyl, 3-methyl-4-ethylhexyl, 3,3,4-trimethylpentyl, 3,4,4-trimethylpentyl, 3,3,4-trimethylhexyl, 3,4,4-trimethylhexyl, 3,3,4,4-tetramethylpentylaldehyd particularly $C_2$-$C_{12}$-n-alkanals.

We particularly prefer to use, as starting materials, acetaldehyde for the preparation of pentaerythritol, propionaldehyde for the preparation of trimethylol ethane, n-BA for the preparation of TMP and n-pentanal for the preparation of trimethylol butane.

Instead of alkanals, use may be made of compounds of the formula IV, eg, acroleins, such as acrylaldehyde (acrolein) 2-methylacrylaldehyd, 2-ethylacrylaldehyd, 2-propylacrylaldehyd, 2-butylacrylaldehyd, 2-pentylacrylaldehyd, 2-isopropylacrylaldehyd, 2-isobutylacrylaldehyd, 2-hexylacrylaldehyd, 2-heptylacrylaldehyd, 2-dodecylacrylaldehyd, 2-pentadecylacrylaldehyd, 2-methoxyacrylaldehyd, 2-ethoxyacrylaldehyd, 2-propoxyacrylaldehyd or 2-butoxyacrylaldehyd. Of these, 2-methylacrolein, 2-ethylacrolein and 2-propylacrolein are preferred. Acrolein may also be used to advantage for the production of pentaerythritol.

As may be seen from the above equation 3, the use of acroleins of the general formula IV as starting material calls for one equivalent less of FA for quantitative conversion to compounds of the formula II than is the case when the corresponding saturated aldehydes are used.

Suitable tert-amines are those which are known to be suitable with regard to the condensation of aldehydes with formaldehyde, such as are described in, eg, DE-A 2,813,201 and DE-A 2,702,582. Particularly preferred tert-amines are tri-n-alkylamines, such as triethylamine, tri-n-propylamine, tri-n-butylamine and particularly trimethylamine.

The process of the invention is characezrized by high yields based both on the aldehyde used and on the formaldehyde and leads to very small losses of amine catalyst. Due to the fact that relatively low pH's are used during the process, no Cannizzaro reaction takes place, and this avoids the formation of formate salts as coupling products.

EXAMPLES

Examples 1 to 4: Batch Method

Example 1

288 g of n-butyraldehyde (4 mol) were stirred with 3000 g of 10% strength formaldehyde (10 mol) and 26 g of 45% strength trimethylamine (0.2 mol) at 25° C. The reaction solution was then found to contain 0.7 mol of n-BA (conversion to n-BA 82.5%) and 0.5 mol of EA (selectivity toward EA 15%). The reaction solution was concentrated by distillation in a Sambay evaporator at 140° c. using a feed of 10 mL/h of low-boilers and water. There were obtained 1195 g of distillate and 2119 g of bottoms, which were again concentrated in the Sambay evaporator. There were formed 795 g of distillate and 1324 g of bottoms. Said bottoms were concentrated for a third time in the Sambay evaporator. There were obtained 494 g of distillate and 830 g of bottoms. The combined distillates (2484 g) were stirred over a period of 5 hours at 30° C. and then again concentrated in the Sambay evaporator (140° C.). This gave 1435 g of bottoms and 1049 g of distillate, which was then processed as described in Example 2.

The combined bottoms (2265 g of DMB solution, pH 4.1) which contained no n-BA or EA, were subjected to continuous hydrogenation. For this purpose the reaction solution was pumped into a tubular reactor together with hydrogen at a pressure of 30 bar tubular reactor heated at 90° C. and packed with 100 mL of a copper on $SiO_2$ catalyst containing 25 wt % of copper, calculated as copper, and 75 wt % of $SiO_2$ and prepared by the process described in WO95/32171. The solution to be hydrogenated was trickled through the catalyst bed and a portion of the still pressurized effluent was recycled to the reactor (recirculating method). Effluent was continuously withdrawn from the reactor at a rate equal to the feed rate, depressurized and collected in a receiver.

The entire hydrogenation effluent was finally distilled. Low-boilers were analyzed by means of quantitative gas chromatography (GC) and medium-boilers, TMP and higher condensation products, comprising oligomers such as ditrimethylol propane or TMP/EA/TMP trimers, were weighed.

|  | MeOH | n-BuOH | Me—BuOH | diol | TMP | higher condensation products |
|---|---|---|---|---|---|---|
| analysis method | GC | GC | GC | weighed | weighed | weighed |
| g | 25.6 | 2.9 | 2.5 | 8.3 | 375 | 8 |
| mol | 0.8 | 0.04 | 0.03 | 0.08 | 2.8 | 0.06 |

(MeOH = methanol; n-BuOH = n-butanol; Me—BuOH = 2-methylbutanol; diol = 3-ethylpropane-1,3-diol; TMP = trimethylol propane; higher condensation products evaluated as TMP equivalents) based on n-BA or FA equivalents in the hydrogenation effluent *)

TMP yield (based on n-BA) 70% 90%
yield (based on FA) 56% 84%

| *) definition of the equivalents | MeOH | n-BuOH | Me—BuOH | diol | TMP | higher condensation products |
|---|---|---|---|---|---|---|
| n-BA | — | 1 | 1 | 1 | 1 | 1 |
| FA | 1 | — | 1 | 1 | 2 | 2 |

Example 2

To the remaining distillate (1049 g) from example 1 there were added 1951 g of an aqueous solution containing 9 mol of FA and 26 g of 45% strength trimethylamine (0.2 mol) and the mixture was stirred for 3 h at 30° C. then 288 g of n-butyraldehyde (4 mol) were added and the mixture stirred for a further 4 h at 30° C. The mixture was then purified by distillation as described in Example 1. There were obtained 873 g of distillate which was processed as described in Example 3 below, and 2441 g of bottoms (DMB solution), which following hydrogenation and distillation in a similar manner to that described in Example 1 gave a product having the following composition:

|  | MeOH | n-BuOH | Me—BuOH | diol | TMP | higher condensation products |
|---|---|---|---|---|---|---|
| analysis method | GC | GC | GC | weighed | weighed | weighed |
| g | 28 | 3 | 3 | 11 | 429 | 10 |
| mol | 0.9 | 0.04 | 0.034 | 0.1 | 3.2 | 0.075 | based on n-BA or FA equivalents in the hydrogenation effluent *)
yield (based on n-BA) 80% 92.7%
yield (based on FA) 71% 84%

Example 3

To the 873 g of distillate of Example 2 there were added 2127g of an aqueous solution containing 9 mol of FA and 26 g of 45% strength trimethylamine (0.2 mol) and the mixture was stired over a period of 3 h at 30° C. 288 g of n-butyraldehyde (4 mol) were then added and the mixture was stirred for a further 4 h at 30° C. and was subsequently purified by distillation as described in Example 1. There were obtained 1096 g of distillate, which was processed as described in Example 4, and 2218 g of DMB solution, which following hydrogenation and distillation gave a product having the following composition:

|  | MH | n-BuOH | Me—BuOH | diol | TMP | higher condensation products |
|---|---|---|---|---|---|---|
| analysis method | GC | GC | GC | weighed | weighed | weighed |
| g | 32 | 2.5 | 4 | 10 | 476 | 15 |
| mol | 1 | 0.033 | 0.045 | 0.096 | 3.55 | 011 | based on n-BA or FA equivalents in the hydrogenation effluent *)
yield (based on n-BA) 88.7% 92.5%
yield (based on FA) 78.8% 84%

Example 4

To the 1096 g of distillate of Example 3 there were first of all added 1904 g of an aqueous solution containing 8.5 mol of FA and 26 g of 45% strength trimethylamine (0.2 mol) and the mixture was stirred for a period of 5 h at 30° C. Then there were added 288 g of n-butyraldehyde (4 mol) and stirring was continued for a further 5 h at 30° C. Following purification by distillation as described in Example 1 there were obtained 1150 g of distillate, which can be processed further. The bottoms containing 2164 g of DMB solution had the following composition after being subjected to hydrogenation and distillation:

|  | MeOH | n-BuOH | Me—BuOH | diol | TMP | higher condensation products |
|---|---|---|---|---|---|---|
| analysis method | GC | GC | GC | weighed | weighed | weighed |
| g | 35 | 2 | 2.5 | 15 | 482 | 20 |
| mol | 1.1 | 0.027 | 0.03 | 0.14 | 3.6 | 0.15 |
|  |  |  | based on n-BA or FA equivalents in the hydrogenation effluent *) | | | |
| yield (based on n-BA) |  | 90% |  |  | 91.2% |  |
| yield (based on FA) |  | 84.7% |  |  | 82% |  |

Cumulation over Examples 1 to 4 gives the following balance

| weight of n-BA used | Weight of FA used | Weight of $NMe_3$ (45%) used |
|---|---|---|
| 1152 g (16 mol) | 9558 g (36.5 mol) | 104 g (0.79 mol) |
| remaining in the distillate (for recirculation): 1.75 equivalents of n-BA and 5.1 equivalents of FA | | |

|  | MH | n-BuOH | Me—BuOH | diol | TMP | higher condensation products |
|---|---|---|---|---|---|---|
| analysis method | GC | GC | GC | weighed | weighed | weighed |
| g | 120.6 | 10.4 | 12 | 44.3 | 1762 | 53 |
| mol | 3.76 | 0.14 | 0.136 | 0.426 | 13.15 | 0.4 |
|  |  |  | based on n-BA or FA equivalents in the hydrogenation effluent *) | | | |
| yield (based on n-BA) |  | 82.2% |  |  | 92.3% |  |
| yield (based on FA) |  | 72% |  |  | 83.7% |  |

Figure 3:
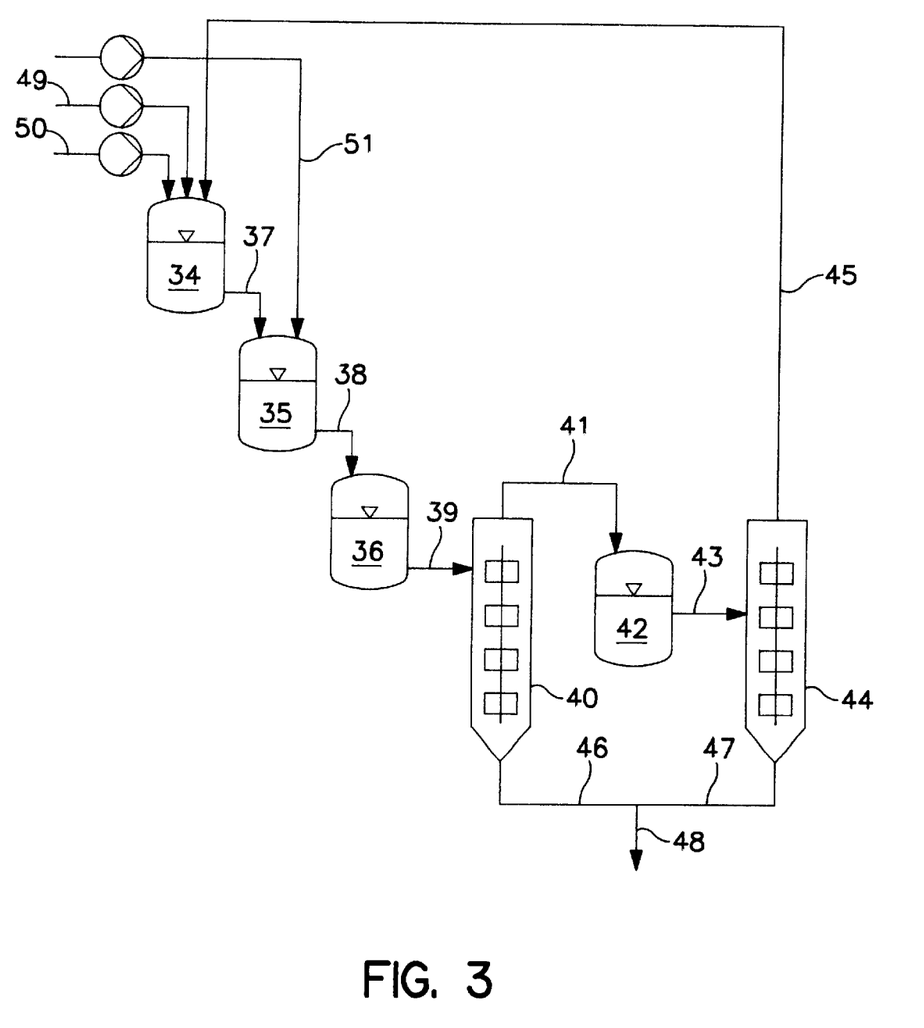
FIGS. 3 and 4 schematically illustrate an apparatus for continuous operation.

The following experiments were carried out in laboratory equipment as diagrammatically illustrated in FIG. 3. The laboratory equipment consisted of a cascade of 3 heated stirred boilers 34, 35 and 36 interconnected by the overflow tubes 37 and 38 and having a capacity of 1000 mL in each case. The overflow of the stirred boiler 36 was passed directly through the overflow tube 39 to the upper region of the Sambay evaporator 40, where it was separated by distillation into low-boiling overheads and high-boiling bottoms. The overheads were passed through pipe line 41 following condensation (not shown) to the post-reactor 42, a heated stirred boiler having a capacity of 500 mL, from which the liquid reaction mixture was passed through the overflow tube 43 directly into the top region of a second Sambay evaporator 44. In the Sambay evaporator 44 the resulting reaction mixture was separated by distillation into low-boiling overheads and high-boiling bottoms and the overheads were recycled through pipe line 45, following condensation (not shown), to the stirred boiler 34 of the cascade. The bottom effluents of the Sambay evaporators 40 and 44 were withdrawn via the pipe lines 46 and 47 and combined and passed through pipe line 48 into a receiver (not shown). The bottom effluents thus collected were processed batchwise as described in the individual examples. The stirred boiler 34 was charged not only via the return stream through pipe line 45 but also through the pipe lines 49 and 50 bringing in FA solution and amine catalyst $NR_3$. n-BA was fed to the stirred boiler 35 through pipe line 51.

Examples 5 to 7: Continuous Operation

Example 5

The apparatus shown in FIG. 3 was charged with the educts as described in table 1 and operated at the temperatures stated. The data referring to MMB, DMB and FA were determined by means of HPLC analysis and were recorded in percentage by weight.

TABLE 1

|  | g in | | MMB | | DMB | | FA | |
|---|---|---|---|---|---|---|---|---|
|  | g/h | 24 h | [%] | [g] | [%] | [g] | [%] | [g] |
| n-BA | 17 | 408 | | | | | | |
| FA | 28.4 | 681.6 | | | | | | |
| $H_2O$ | 66.3 | 1590 | | | | | | |
| $NMe_3$ | 0.6 | 16.8 | | | | | | |
| $H_2O$ | 1.55 | 3.72 | | | | | | |
| Feedback | 204 | 4896 | | | | | | |
| Effluent line 46 | 31.9 | 765 | | | | | | |
| Effluent line 47 | 82 | 1969 | | | | | | |
| Σ effluents lines 46 + 47 | | 2734 | 1.9 | 52.2 | 24.8 | 680 | 13 | 357 |
| Yield | based on n-BA | 9 | | 91 | | | | |
|  | based on FA | 2.25 | | 45.4 | | | 52.4 | |
| Equipment | R34 | R35 | R36 | R42 | S40 | S44 | | |
| T [° C.] | 30 | 31 | 45 | 45 | 155 | 125 | | |

R = stirred boiler  S = Sambay evaporator

The effluent from pipe line 48 (2734 g) was collected and batchwise distilled under atmospheric pressure until 1025 g of bottoms and 1709 g of distillate had been obtained. The low-boiling distillate containing 297 g of formaldehyde was recycled to the stirred boiler 34. This amount of formaldehyde can be deducted from the amount given in Table 1 for balancing purposes.

The bottom products thus combined were hydrogenated as described in Example 1 and the effluent distilled:

|  | MeOH | n-BuOH | Me—BuOH | diol | TMP | higher condensation products |
|---|---|---|---|---|---|---|
| analysis method | GC | GC | GC | weighed | weighed | weighed |
| g | 62 | — | 2.5 | 47 | 678 | 14 |
| mol | 2.06 | — | 0.03 | 0.45 | 5.06 | 0.1 | yield (based on n-BA) 89.3%  yield (based on FA incl. feedback) 78.9%

Example 6

The apparatus illustrated in FIG. 3 was charged with the educts as described in Table 2 and operated at the temperatures stated.

TABLE 2

|  | g in | | MMB | | DMB | | FA | |
|---|---|---|---|---|---|---|---|---|
|  | g/h | 24 h | [%] | [g] | [%] | [g] | [%] | [g] |
| n-BA | 25 | 600 | | | | | | |
| FA | 26.1 | 626.4 | | | | | | |
| $H_2O$ | 66.3 | 1462 | | | | | | |
| $NMe_3$ | 1 | 24 | | | | | | |
| $H_2O$ | 1.2 | 28.8 | | | | | | |
| Reflux | 200 | 4800 | | | | | | |
| Effluent line 46 | 39.5 | 947 | | | | | | |

TABLE 2-continued

| | g/h | g in 24 h | MMB [%] | MMB [g] | DMB [%] | DMB [g] | FA [%] | FA [g] |
|---|---|---|---|---|---|---|---|---|
| Effluent line 47 | 74.8 | 1794 | | | | | | |
| Σ effluents lines 46 + 47 | | 2741 | 2.4 | 65 | 37.2 | 1020 | 5.1 | 140 |
| Yield based on n-BA | | | 7.6 | | 92.4 | | — | |
| based on FA | | | 3 | | 73.7 | | 22 | |
| Equipment | R34 | R35 | R36 | R42 | S40 | S44 | | |
| T [° C.] | 35 | 35 | 50 | 40 | 155 | 125 | | |

R = stirred boiler S = Sambay evaporator

The effluent from pipe line 48 (2741 g) was continuously pumped at a rate of 15 mL/h through a Sambay evaporator (150° C., atmospheric pressure). There were obtained 1506 g of bottoms and 1235 g of distillate. The distillate, which contained 105 g of formaldehyde, was recycled to the stirred boiler 34. To calculate the yield, this amount of formaldehyde must be deducted from the amount given in Table 2.

The bottom products thus combined were hydrogenated as described in Example 1 and the effluent distilled:

| | MH | n-BuOH | Me—BuOH | diol | TMP | higher condensation products |
|---|---|---|---|---|---|---|
| analysis method | GC | GC | GC | weighed | weighed | weighed |
| g | 38 | — | 5 | 60 | 1022 | 14 |
| mol | 1.2 | — | 0.057 | 0.58 | 7.6 | 0.1 | yield (based on n-BA) 91.2% yield (based on FA incl. feedback) 87.4%

Example 7

The apparatus shown in FIG. 3 was charged with the educts as described in Table 3 and operated at the temperatures stated.

TABLE 3

| | g/h | g in 24 h | MMB [%] | MMB [g] | DMB [%] | DMB [g] | FA [%] | FA [g] |
|---|---|---|---|---|---|---|---|---|
| n-BA | 50 | 1200 | | | | | | |
| FA | 62.5 | 1500 | | | | | | |
| H₂O | 187.5 | 4500 | | | | | | |
| NMe₃ | 1.64 | 39.4 | | | | | | |
| H₂O | 2 | 48 | | | | | | |
| Reflux | 345 | 8280 | | | | | | |
| Effluent line 46 | 104.2 | 2500 | | | | | | |
| Effluent line 47 | 199.4 | 4785 | | | | | | |
| Σ effluents lines 46 + 47 | | 7285 | 2.8 | 204 | 26.2 | 1936 | 7.7 | 560 |
| Yield based on n-BA | | | 12 | | 88 | | — | |
| based on FA | | | 4 | | 58.6 | | 37.3 | |
| Equipment | R34 | R35 | R36 | R42 | S40 | S44 | | |
| T [° C.] | 34 | 37 | 46 | 50 | 165 | 140 | | |

R = stirred boiler S = Sambay evaporator

The collected combined effluents from the pipe lines 46 and 47 (7285 g) were stirred with 43 g of 45% strength trimethylamine solution at 40° C. over a period of 3 h. By this means the content of MMB was caused to sink to 1% and that of DMB to rise to 28.7%. The post-reaction solution was then continuously pumped through a Sambay evaporator (150° C., atmospheric pressure) at a rate of 15 mL/h. There were obtained 4027 g of bottoms and 3301 g of distillate. The distillate, which contained 480 g of formaldehyde, was recycled to the stirred boiler 34. This amount of formaldehyde can be deducted from that given in Table 3.

The bottoms thus obtained were hydrogenated as described in Example 1 and the effluent distilled.

| | MH | n-BuOH | Me—BuOH | diol | TMP | higher condensation products |
|---|---|---|---|---|---|---|
| analysis method | GC | GC | GC | weighed | weighed | weighed |
| g | 89 | — | 17.5 | 97 | 2010 | 67 |
| mol | 2.8 | — | 0.2 | 0.93 | 15 | 0.5 | yield (based on n-BA) 90% yield (based on FA incl. feedback) 88%

Example 8

Figure 4:
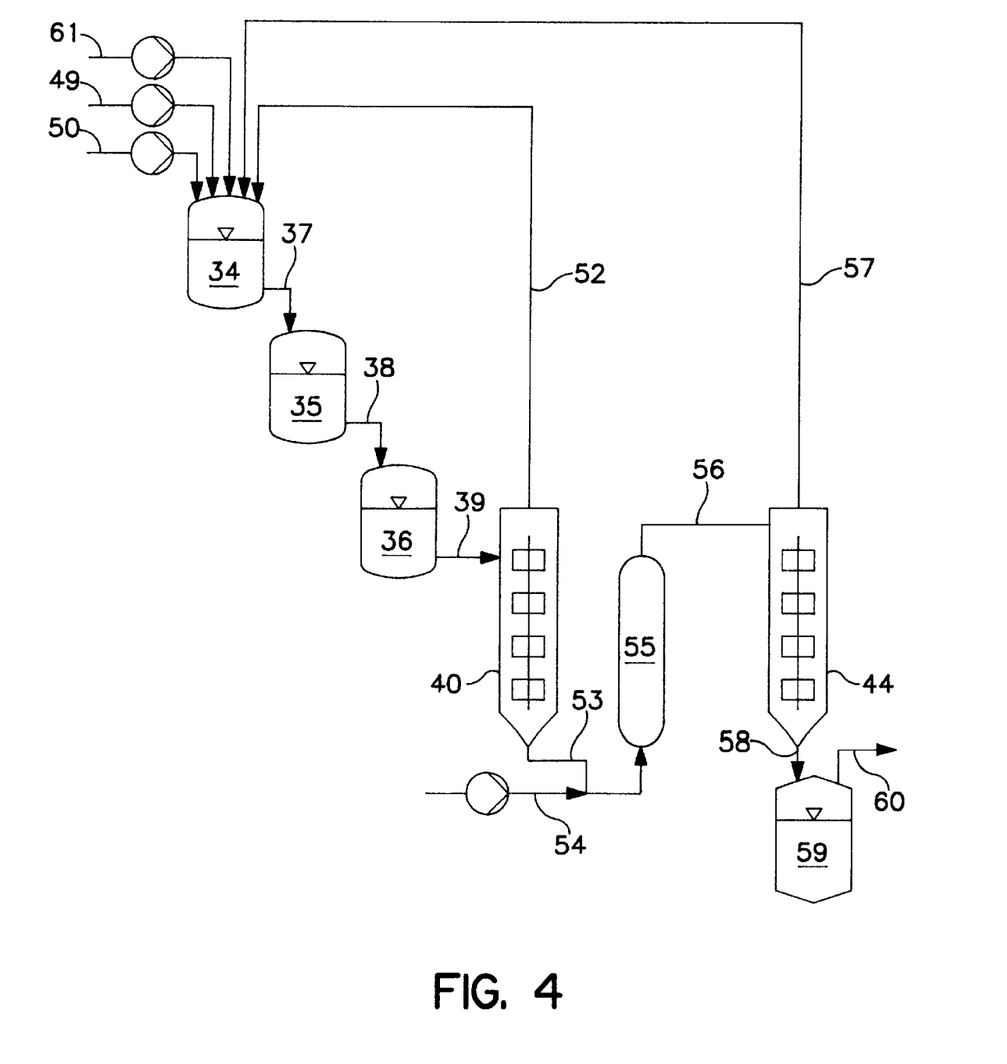

To carry out this example, alterations were made to the laboratory equipment used for Examples 5 to 7, as shown diagrammatically in FIG. 4. The altered laboratory equipment consisted of the cascade of stirred boilers 34, 35 and 36 and the overflow tubes 37, 38 and 39 and the Sambay evaporator 40, all already described with reference to Examples 5–7. The overflow from the stirred boiler 36 was passed through the overflow tube 39 directly to the top region of the Sambay evaporator 40, where it was separated by distillation into low-boiling overheads containing as essential components n-BA, FA, EA, water and trimethylamine and high-boiling bottoms. The overheads were continuously recycled through pipe line 52, following condensation (not shown), to the stirred boiler 34. The high-boiling bottoms from the Sambay evaporator 40 were, following the addition of fresh trimethylamine catalyst (45% strength aqueous solution) via pipe line 54, continuously fed, via pipe line 53, to the post-reactor 55, a heated tubular reactor containing packing material (2.5 mm Raschig rings) and having a capacity of 1000 mL. The effluent from the post-reactor 55 was continuously fed through pipe line 56 into the top region of the Sambay evaporator 44, where it was separated by distillation into low-boiling overheads consisting substantially of EA, FA, trimethylamine and water and high-boiling bottoms. The low-boiling overheads, following condensation (not shown), were continuously recycled through pipe line 57 to the stirred boiler 34, whereas the high-boiling bottoms were collected, via pipe line 58, in a receiver 59, from which they were withdrawn via pipe line 60 for subsequent hydrogenation. The stirred boiler 34 was continuously charged not only with the recirculating streams entering through pipe line 52 and pipe line 57 but also with fresh FA solution and n-BA entering through the pipe lines 49 and 61 respectively and with fresh trimethylamine catalyst in the form of a 45% strength aqueous solution entering through pipe line 50.

The amounts of educts and catalyst introduced are listed in Table 4 together with the amounts of the bottom effluents from the Sambay evaporators 40 and 44 and the composition of the latter effluents. The concentrations of MMB, DMB and FA were determined by means of HPLC and are given in percentages by weight. The temperatures used in the individual stirred boilers and Sambay evaporators are likewise given in Table 4. The distillation in the Sambay evaporators was carried out under atmospheric pressure.

TABLE 4

| Feed via Pipe line | | g/h | g in 24 h | MMB [%] | [g] | DMB [%] | [g] | FA [%] | [g] |
|---|---|---|---|---|---|---|---|---|---|
| 61 | n-BA | 50 | 1200 | | | | | | |
| 49 | FA | 57.3 | 1275 | | | | | | |
| | H$_2$O | 133.5 | 3208 | | | | | | |
| 50 | NMe$_3$ | 1.02 | 24.5 | | | | | | |
| | H$_2$O | 1.25 | 30 | | | | | | |
| 54 | NMe$_3$ | 1.02 | 24.5 | | | | | | |
| | H$_2$O | 1.25 | 30 | | | | | | |
| | Bottom effluent S40 | 500 | 12000 | | | | | | |
| | Bottom effluent S40 | 245.3 | 5888 | 0.5 | 29 | 35.5 | 2090 | 7 | 415 |
| | Yield based on n-BA | | | 1.7 | | 95 | | — | |
| | based on FA | | | 0.62 | | 69 | | 30.2 | |
| | Equipment | R34 | R35 | R36 | R55 | S40 | | S44 | |
| | T [° C.] | 35 | 50 | 60 | 55 | 140 | | 140 | |

R = stirred boiler  S = Sambay evaporator

The bottoms in the receiver 59 were hydrogenated as described in Example 1 and the effluent was distilled:

| | MH | n-BUOH | Me—BuOH | diol | TMP | higher condensation products |
|---|---|---|---|---|---|---|
| analysis method | GC | GC | GC | weighed | weighed | weighed |
| g | 445 | — | 10 | 40 | 2077 | 25 |
| mol | 13.9 | — | 0.11 | 0.4 | 15.5 | 0.19 | yield (based on n-BA) 93% yield (based on FA) 68%

We claim:

1. A process for the preparation of a methylolalkanal of the formula II (II)

wherein R is a methylol group or an alkyl group of from 1 to 22 carbon atoms or an aryl of aralkyl group of from 6 to 22 carbon atoms, by condensation of aldehyde having from 2 to 24 carbon atoms with formaldehyde and a tertiary amine catalyst, which process is carried out step-wise and comprises a) in a first step, reacting the aldehyde with 2 to 8 times the molar amount of formaldehyde in the presence of the tertiary amine, b) in a second step, separating the reaction mixture
  i) into a bottom fraction comprising, in addition to the compounds of formula II, an incompletely methylolated compound of the formula III

(III)

and a distillate stream comprising unconverted or partially converted starting materials, or ii) into an aqueous phase and an organic phase, by means of a phase-separating equipment, and recycling the distillate stream or the organic phase to the first stage, and c) in a third stage, subjecting the bottom fraction or the aqueous phase
  i) to a catalytic reaction or thermal reaction, to convert the compound of the formula III to the compound of formula II and to a corresponding methylene compound of formula IV (IV)

wherein R' is hydrogen or the radical R, and ii) distilling the reaction product, wherein an overhead stream comprising the compound of the formula IV and unconverted formaldehyde is recycled to the first stage, and the compound of the formula II is isolated from the bottom fraction.

2. The process defined in claim 1, wherein the distillate or organic phase recovered from stage b) is reacted with formaldehyde and a tertiary amine prior to reacting it with the aldehyde in stage a).

3. The process defined in claim 1, wherein the distillate of stage $c_{ii}$) is repeatedly recycled to stage $c_i$) before being recycled to stage a).

4. The process defined in claim 1, wherein the aldehyde is propionaldehyde or n-butyraldehyde.

5. The process defined in claim 1, wherein the aldehyde is acetaldehyde.

6. The process defined in claim 1, which is carried out continuously.

7. The process defined in claim 1, wherein the tertiary amine catalyst is employed in an amount sufficient for the reaction mixture to have a pH of from 5 to 12.

8. The process defined in claim 1, wherein the tertiary amine is trimethylamine.

9. The process defined in claim 1, wherein the same catalyst is used in stages a) and c).

10. The process defined in claim 1, wherein the aldehyde is partially or completely replaced by the corresponding compound of formula III.

11. The process defined in claim 1, wherein the first stage a) is carried out in a tubular reactor or a cascade of stirred vessels.

12. The process defined in claim 1, wherein stage c) is carried out in a tubular reactor or a cascade of stirred vessels.

13. A process for the preparation of a polymethylol compound of the formula I (I)

wherein R is a methylol group or an alkyl group containing from 1 to 22 carbon atoms or an aryl of aralkyl group containing from 6 to 22 carbon atoms, which process comprises first preparing a methylolalkanal of the formula (II)

in accordance with the process defined in claim 1, then hydrogenating the methylolalkanal of the formula II prepared in the first stage, and subsequently recovering the polymethylol compound of formula I.

14. The process defined in claim 13 for the preparation of trimethylol ethane or trimethylol propane.

15. The process defined in claim 13 for the preparation of pentaerytritol.

* * * * *